United States Patent [19]

Gilhaus

[11] Patent Number: 4,537,207
[45] Date of Patent: Aug. 27, 1985

[54] CALLOUS-REMOVING SKIN-FILE

[75] Inventor: Heinz Gilhaus, Solingen, Fed. Rep. of Germany

[73] Assignee: Firma Credo Stahlwarenfabrik Gustav Kracht, Solingen, Fed. Rep. of Germany

[21] Appl. No.: 479,801

[22] Filed: Mar. 28, 1983

[30] Foreign Application Priority Data

Apr. 2, 1982 [DE] Fed. Rep. of Germany ....... 3212274
Apr. 29, 1982 [GB] United Kingdom ................ 8212519

[51] Int. Cl.³ ............................................. A45D 29/20
[52] U.S. Cl. .................................... 132/76.4; 128/304; 132/76.5
[58] Field of Search .................... 132/76.4, 76.2, 75.6, 132/76.5; 51/380, 29, 78, 80, 76 R; 128/303.14, 304, 355

[56] References Cited

U.S. PATENT DOCUMENTS 2,898,914 8/1959 Särdal ................................. 128/304
3,198,198 8/1965 Bittner ............................... 132/76.4
3,339,562 9/1967 Rowe ................................. 132/76.5

FOREIGN PATENT DOCUMENTS 920960 3/1963 United Kingdom .............. 132/76.4

Primary Examiner—Gregory E. McNeill
Attorney, Agent, or Firm—Holman & Stern

[57] ABSTRACT

A skin-file or rasp of the kind comprising a gripping handle (1) which is provided at one end with a rasp head (2), the latter removably holding a rasping foil (11) which has longitudinally extending edges (10) having inturned portions which embrace the longitudinally extending edges of the rasp head. The edges of the rasp head are thickened and are provided with grooves (6) in which the longitudinal edges (10) of the rasping foil are located, the rasp head being provided at each end with an end stop (8 and 9) to prevent longitudinal movement of the rasping foil relative to the rasp head. The rasping foil is also provided on each of its longitudinal edges with narrow, outwardly projecting portions (12) which assist in engaging or disengaging the rasping foil from the rasp head.

17 Claims, 5 Drawing Figures

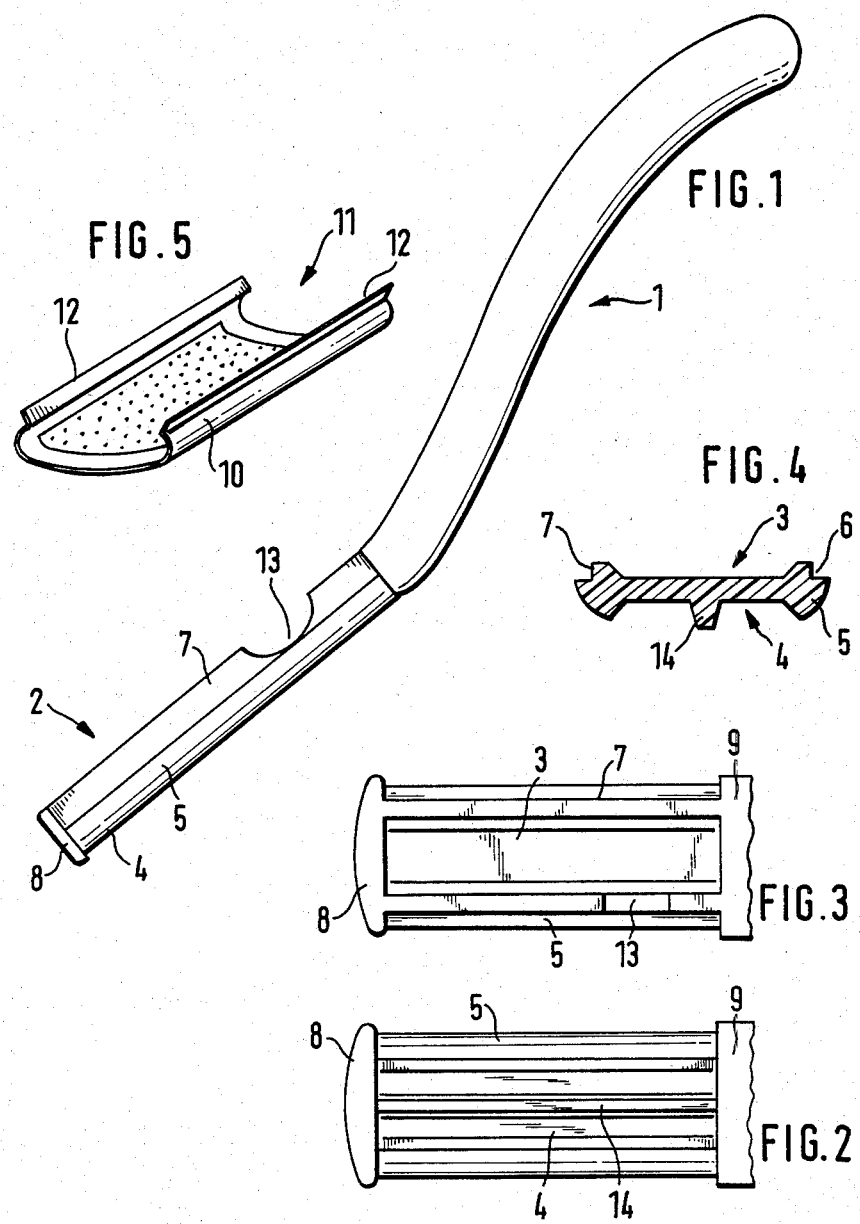

CALLOUS-REMOVING SKIN-FILE

BACKGROUND OF THE INVENTION

1. Field of the Invention

The invention relates to a callous-removing skin-file or rasp of the kind comprising a handle, a rasp head and a rasping foil which is mounted on the rasp head.

2. Description of the Prior Art

A skin-file of this kind is described in German Pat. No. 19 85 681. In this known file the rasp head consists of an arched plate of a thin material and a filing or rasping foil can be slid over this plate. The sliding direction is in the direction of the length of the gripping handle and coincides with the direction of working at any rate when as is most frequently customary the rasping or filing action is produced by sliding the handle forwards and back. In the course of this kind of manipulation the arched plate which supports the rasping file may easily be pushed out of the rasping foil when the handle is pushed backwards so that trouble-free rasping or filing action can only be obtained during the forward sliding of the skin-file because then the arched plate is arrested by a rearwardly angled leading edge of the rasping foil.

BRIEF SUMMARY OF THE INVENTION

Starting with this known arrangement it is the basic aim of the present invention to develop the known skin-file further in the sense that it may be unrestrictedly used and applied in any direction of working. Particularly the effective application of the file in the preferred direction of working, that is to say by pushing the file forwards and back, is no longer accompanied by the risk of accidentally detaching the rasp head from the rasping foil, file manipulation in a vertical direction relative to this movement is also made easier and, lastly, the rasping foil which is liable to clog up in use, is made easily removable for cleaning. Over and above this, provision is made for the abraded hard skin particles which pass through the rasping foil to be accommodated or picked up without compacting in the gap between the rasp-head and rasping foil and eventually being very hard to scrape off one or the other of these parts.

In accordance with the invention, there is provided a callous-removing skin file, or rasp, comprising a rasp head arranged at the end of a gripping handle and having its effective underside provided with a filing or rasping foil whose longitudinally extending edges have inturned portions which embrace the longitudinally extending edges of the rasp head extending parallel to the length of the handle, characterised in that the longitudinally extending edges of the rasp head are thickened, adjoining which edges the rasp head has grooveways which are bounded by limiting web regions as well as being bounded by projecting end stops at both ends of the rasp head, and in that narrow, outwardly angled zones are provided on said longitudinally extending edges of the rasping foil.

In the new skin-file the projecting end stops at the ends of the rasp head ensure that the rasping foil can no longer slide in the longitudinal direction of the handle so that there is no longer any risk of separation between rasping foil and rasp head when the skin-file is worked longitudinally in either direction. Furthermore, by virtue of the thickened longitudinal edges or beads the rasping foil can be introduced by one bent-back edge into a groove-way on one side whereupon the opposite edge is pressed on until it also snaps into place in the groove-way on the opposite side of the head. The provision of the outwardly angled zones next to the incurving edges of the foil enables the rasping foil to be tensioned by one finger so that it can be equally easily disengaged again from the rasp head when required. Critical for this effect is the fact that the rasping foil is made of steel, in the customary fashion, which has the required elastic properties. The abutment of the rasping foil edges against the limiting web region of the head ensures a precise fit or seat of the foil on the rasp head so that the rasp movements are precisely transmitted. This very largely precludes the risk of accidental injuries.

Furthermore, with the kind of mutual connection between rasp head and rasping foil provided according to this invention it is also practically possible that in the event of a file movement transversely to the longitudinal direction the side edges of the rasping foil lift off the longitudinal edges.

The operations of fitting and removing the rasping foil are facilitated by the fact that the longitudinal edges of the rasp head are not only thickened but also rounded. Furthermore, the disengagement of the edge of a rasping foil from its groove-way may be further facilitated by providing a depression in the latter in which a fingertip may be inserted to apply pressure to the marginal zone of the rasping foil.

Whereas the rasping foil consists of a steel with sufficient elasticity, as already mentioned, the rasp head consists conveniently of a plate of plastics material provided with multiple reinforcements designed to prevent bending directions. Preferably the plastics plate which constitutes the rasp head is further provided with a central longitudinal rib which at the same time provides support for the rasping foil. In this way, when the rasping foil is fitted on the rasp head, two longitudinally extending compartments or chambers relatively separated by such a longitudinal rib are formed between foil and rasp head. This not only affords an overall low-mass design for the rasp head as a whole enabling it to be produced relatively distortion free from a given plastics material, but also creates suitable spaces for the accommodation of the abraded hard skin particles which pass through the rasping foil without risk of incrustations building up as in the known skin-file. An appropriate reinforcing effect is provided by the relatively thick (in cross-section) longitudinal edges and limiting webs and central longitudinal rib compared to which the remaining regions of the rasp head may be considerably thinner in cross-section.

Conveniently the rasp head and the gripping handle are manufactured together in one piece from the plastics material. This allows the projecting shoulder between the rasp head and handle to be designed as an integral part of the gripping handle.

BRIEF DESCRIPTION OF THE DRAWINGS

The invention is more particularly described with reference to an embodiment illustrated by way of example in the accompanying drawings wherein:

FIG. 1 is a side elevational view of the new skin-file of this invention,

FIG. 2 is a bottom plan view of the underside of the rasp head of FIG. 1,

FIG. 3 is a top plan view of the topside of the rasp head of FIG. 1,

FIG. 4 is a cross-sectional view of the rasp head

FIG. 5 is a perspective view of the rasping foil according to the invention.

DETAILED DESCRIPTION

FIG. 1 shows the gripping handle 1 molded in one piece with the rasp head 2 and formed of a plastics material. The handle 1 is shaped to fit comfortably in the hand of the user. The rasp head 2 extends in the longitudinal direction of the handle. Its effective, or 'working', underside 4 receives a rasping foil 11, the inturned outer edges 10 of which enter into grooveways 6 formed in the thickened longitudinal edges of the head and engage with limiting web regions or flanges 7 thereof. The outwardly angled zones 12 along the edges of the foil will then project slightly along the sides of the rasp head.

In order to prevent sliding displacement of the rasping foil 11 in the longitudinal direction a first projecting end stop 8 is provided at the leading end of the rasp head 2 whilst a second end stop 9 is provided at the rear end, namely at the point of junction with the gripping handle 1.

The relative distance between these two end stops 8 and 9 corresponds to the length of the rasping foil 11. The underside of the rasp head is also formed integrally with a longitudinal rib 14 which in use engages the upper side of the rasping foil and provides support therefor.

The rasping foil 11 is located in the transverse direction relative to its length by the snap-fit of its inwardly curved longitudinally extending edges 10 over the longitudinal edges 5 of the rasp head which are rounded. For removal of the rasping foil the user inserts the tip of a finger into the finger-hold depression 13 provided for this purpose and applies pressure to the adjacent outer zone 12 of the rasping foil 11. This causes the foil to lift off the top side 3 of the rasp head 2 whereupon it can be twisted further and eventually completely detached from the rasp head.

I claim:

1. A callous-removing skin file, or rasp, comprising:
   a longitudinally extending gripping handle having an inner and an outer end;
   a rasp head extending from the inner end of said handle having an upper side, a lower side, and longitudinal edges extending parallel to the longitudinal axis of said handle, said longitudinal edges being thicker than the part of the rasp head between said edges;
   grooveways in and extending substantially parallel to and along the outer sides of said longitudinal edges;
   flanges along said edges forming limiting inner shoulder portions of said grooveways;
   projecting shoulder portions at both ends of said rasp head forming end stops;
   a filing or rasping foil member removably attached to said rasp head having a cutting surface and longitudinal edges with inturned portions releasably engaged in said grooveways in abutting relationship along the edges thereof with said flanges and at the ends thereof with said end stops so that said foil member is retained on and in fixed embracing relationship with said rasp head during use; and outwardly angled flanges along the edges of said foil member of the rasp.

2. A skin-file according to claim 1 wherein said inturned portions of said longitudinal edges of the foil member are rounded.

3. A skin-file according to claim 1 and further comprising: a recess in one of said flanges on the edges of said rasp head along a grooveway for the insertion therein of a fingertip in order to press outwardly one of the outwardly angled flanges on the edges of the rasping foil.

4. A skin-file according to claim 1 wherein said rasp head comprises a substantially planar member of plastics material which is reinforced along its marginal sides by said thickened longitudinally extending edges and said flanges thereon and further comprising a central longitudinal rib on said lower side of said rasp head which supports the rasping foil and additionally reinforces said rasp head.

5. A skin-file according to claim 4, wherein said flanges, longitudinal edges and, central longitudinal rib of the rasp head are all greater in cross-sectional thickness than the remainder of the rasp head.

6. A skin-file according to claim 1 wherein the rasp head and the gripping handle are formed in one piece from a plastics material.

7. A skin file as claimed in claim 1 wherein said grooveways extend along the outer upper side of said longitudinal edges of said rasp head.

8. A skin file as claimed in claim 1 wherein said outer lower portions of said longitudinal edges of said rasp head are rounded.

9. A skin file as claimed in claim 7 wherein said outer lower portions of said longitudinal edges of said rasp head are rounded.

10. A skin file as claimed in claim 9 wherein the longitudinal edges of said foil member are rounded and substantially conform to said rounded portions of said longitudinal edges of said rasp head.

11. A skin file as claimed in claim 10 wherein said flanges project from said upper side of said rasp head.

12. A skin file as claimed in claim 1 wherein said flanges project from said upper side of said rasp head.

13. A skin file according to claim 11 wherein said rasp head comprises a substantially planar member of plastics material which is reinforced along its marginal sides by said thickened longitudinally extending edges and said flanges thereon and further comprising a central longitudinal rib on said lower side of said rasp head which supports the rasping foil and additionally reinforces said rasp head.

14. A skin file according to claim 11, wherein said flanges, longitudinal edges and central longitudinal rib of the rasp head are all greater in cross-sectional thickness than the remainder of the rasp head.

15. A skin file according to claim 11, wherein the rasp head and the gripping handle are formed in one piece from a plastics material.

16. A skin file as claimed in claim 10, wherein said foil member is resilient at least in the direction transverse to its longitudinal axis so that it engages onto said rasp head by a snap-fit engagement.

17. A skin file as claimed in claim 15, wherein said foil member is resilient at least in the direction transverse to its longitudinal axis so that it engages onto said rasp head by a snap-fit engagement.

* * * * *